United States Patent
Yan et al.

(10) Patent No.: US 12,339,270 B1
(45) Date of Patent: Jun. 24, 2025

(54) NEURAL NETWORK-BASED WATER QUALITY MONITORING DEVICE FOR MARINE RANCH AND DEPLOYMENT METHOD THEREOF

(71) Applicant: Guangdong Ocean University., Zhanjiang (CN)

(72) Inventors: Yunrong Yan, Zhanjiang (CN); Kun Zhang, Zhanjiang (CN); Chengqi Sun, Zhanjiang (CN); Shoujun Zhang, Zhanjiang (CN); Banglin Deng, Zhanjiang (CN); Yin Sun, Zhanjiang (CN); Wei Wang, Zhanjiang (CN)

(73) Assignee: Guangdong Ocean University, Zhanjiang (CN)

( * ) Notice: Subject to any disclaimer, the term of this patent is extended or adjusted under 35 U.S.C. 154(b) by 0 days.

(21) Appl. No.: 19/070,900

(22) Filed: Mar. 5, 2025

(30) Foreign Application Priority Data

Jul. 22, 2024 (CN) .......................... 202410982589.3

(51) Int. Cl.
*G01N 33/18* (2006.01)
*G01N 21/31* (2006.01)
(Continued)

(52) U.S. Cl.
CPC ..... *G01N 33/1886* (2013.01); *G01N 21/3103* (2013.01); *B63B 2022/006* (2013.01); *G01N 2021/3133* (2013.01); *G16C 20/70* (2019.02)

(58) Field of Classification Search
CPC ............... G01N 21/31; G01N 21/3103; G01N 2021/3129; G01N 2021/3133;
(Continued)

(56) References Cited

U.S. PATENT DOCUMENTS

| | | | | |
|---|---|---|---|---|
| 2004/0233447 A1* | 11/2004 | White | ..................... | G01N 21/31 356/417 |
| 2016/0122201 A1* | 5/2016 | Gilmore | ................. | G01N 21/33 702/30 |

(Continued)

FOREIGN PATENT DOCUMENTS

CN 115144331 A * 10/2022

OTHER PUBLICATIONS

Machine Translation of CN 115144331 (Year: 2022).*
(Continued)

*Primary Examiner* — Nathaniel J Kolb
(74) *Attorney, Agent, or Firm* — Hemisphere Law, PLLC; Zhigang Ma

(57) ABSTRACT

A neural network-based water quality monitoring device for a marine ranch includes a floating board and a host computer monitor. The host computer monitor is disposed on a top of the floating board, and the host computer monitor is provided with a water quality monitoring system, and the water quality monitoring system is configured to collect water quality parameters of the marine ranch and analyze collected water quality parameters. The environmental monitoring unit is configured to use a hyperspectral water quality multiparameter monitor to monitor continuous spectral segments within a target wavelength range in water body in the marine ranch to monitor in real time data including a concentration of dissolved substances in the water, growth of algae, water pollution, water color, and presence of solid floating objects on water surface. The device can apply multiple water quality tests to improve the effectiveness and accuracy of water quality monitoring.

9 Claims, 11 Drawing Sheets

(51) Int. Cl.
*B63B 22/00* (2006.01)
*G16C 20/70* (2019.01)

(58) Field of Classification Search
CPC ........ G01N 2021/3137; G01N 33/1886; B63B 2022/006
See application file for complete search history.

(56) References Cited

U.S. PATENT DOCUMENTS

2021/0033589 A1* 2/2021 Tufillaro ............... G01J 3/0289
2021/0161089 A1* 6/2021 Haverkamp ......... A01K 63/065
2021/0389243 A1* 12/2021 Sela ........................ C12Q 1/04

OTHER PUBLICATIONS

Xing, Xufeng, et al., Development of a comprehensive monitoring system on environmental information in sea ranching, Journal of Dalian Ocean University, 02, 2017, pp. 105-110.
CNIPA, Notification of First Office Action for CN202410982589.3, Aug. 23, 2024.
Guangdong Ocean University (Applicant), Replacement claims (allowed) of CN202410982589.3, Aug. 27, 2024.
CNIPA, Notification to grant patent right for invention in CN202410982589.3, Sep. 5, 2024.

* cited by examiner

NEURAL NETWORK-BASED WATER QUALITY MONITORING DEVICE FOR MARINE RANCH AND DEPLOYMENT METHOD THEREOF

CROSS-REFERENCE TO RELATED APPLICATION

This application claims priority to Chinese Patent Application No. 202410982589.3, filed Jul. 22, 2024, which is herein incorporated by reference in its entirety.

TECHNICAL FIELD

The disclosure relates to the technical field of water quality testing, and particularly to a neural network-based water quality monitoring device for a marine ranch and a deployment method thereof.

BACKGROUND

With the continuous development and utilization of marine resources, marine ranching, as an important form of marine fisheries, faces significant challenges in water quality conditions that critically impact distribution and growth of aquatic organisms. These conditions are key factors determining a yield and quality of marine ranching. However, existing water quality monitoring devices exhibit certain limitations, including long measurement cycles, high costs, and limited monitoring coverage. Additionally, the existing water quality monitoring devices fail to analyze inherent relationships among monitored data, resulting in low efficiency in water pollution detection.

The defects of the existing water quality monitoring devices are as follows.

1. In the Chinese patent with a publication number of CN219475587U, a primary focus is on resolving the problem that existing water quality monitoring and alarm devices lack effective self-cleaning functions, without addressing the failure of current water quality monitoring apparatuses to analyze intrinsic relationships between monitored data points during operation, resulting in compromised detection efficacy and accuracy.

2. In the Chinese patent application with a publication number of CN114596167A, the primary focus is on addressing the problem of information acquisition delay, while failing to consider that existing water quality monitoring devices cannot integrate multi-source data during operation, resulting in poor monitoring effectiveness.

3. In the Chinese patent application with a publication number of CN118033077A, the primary focus is on how to expand the scope of water quality detection and prolong the service life of the device. However, it fails to address the issues of poor sampling convenience during operation and the inability to simultaneously acquire data and collect water samples from multiple sampling points within a short time frame.

4. In the Chinese patent with a publication number of CN105606404A, the primary focus is on improving the accuracy of water sample detection. However, it fails to address an inability of existing water quality monitoring devices to be deployed according to size and shape of marine ranching areas, nor does it consider the poor interconnection convenience between devices.

SUMMARY

The purpose of the disclosure is to provide a neural network-based water quality monitoring device for marine ranch and a deployment method thereof, in order to solve the problems raised in the background mentioned above.

To achieve above purpose, the technical solutions of the disclosure are as follows.

A neural network-based water quality monitoring device for marine ranch includes a floating board and a host computer monitor. The host computer monitor is disposed on a top of the floating board, and the host computer monitor is provided with a water quality monitoring system, and the water quality monitoring system is configured to collect water quality parameters of the marine ranch and analyze the collected water quality parameters. The water quality monitoring system includes an environmental monitoring unit, a data acquisition unit, a wireless transmission unit, and a data integration unit. The environmental monitoring unit is configured to use a hyperspectral water quality multiparameter monitor to monitor continuous spectral segments within a target wavelength range in water body in the marine ranch to monitor in real time data including a concentration of dissolved substances in the water body, growth of algae, water pollution, water color, and presence of solid floating objects on a water surface of the marine ranch. The data acquisition unit is configured to use a data collector to collect the monitored data monitored from the environmental monitoring unit. The wireless transmission unit includes a coordinator, and the coordinator is configured to upload the collected data to a neural network for analysis and processing. The data integration unit is configured to use a central processor to accumulate and integrate data generated during an operation of the marine ranch, and employs cloud computing technology to conduct in-depth analysis and mining of the intrinsic relationships and objective laws among various objectives in the marine ranch. Connection mechanisms are uniformly distributed on a bottom of the floating board, a bottom of each of the connection mechanisms is provided with s placement board. A top of the placement board is provided with two water quality parameter detection mechanisms symmetrically arranged, and the two water quality parameter detection mechanisms are disposed at two sides of the connection mechanism. A back side of the two water quality parameter detection mechanisms is provided with a sampling mechanism, and the sampling mechanism is configured to collect water samples from different time periods. The sampling mechanism includes a hook ring disposed on an outer surface of the floating board, a top of the floating board is provided with positioning rods, and the positioning rods are disposed at an outer side of the host computer monitor. A longitudinal section shape of each of the positioning rods is T-shaped, and outer surfaces of the positioning rods are wound with connecting ropes, an end of a corresponding one of the connecting ropes passes through the hook ring and is connected to a sampling bucket. A bottom of the sampling bucket defines a sampling hole, a mesh plate is disposed in the sampling hole. The bottom of the sampling bucket defines a groove, and the groove is connected to the sampling hole. A sealing plug is disposed in the groove, a bottom of the sealing plug is in contact with a top of the mesh plate. A perforated baffle is disposed in the sampling bucket, and the perforated baffle is configured to position the sealing plug. A bottom of the sealing plug is embedded with a first electromagnet, the bottom of the groove is embedded with a first iron block, and a top of the first iron block is in contact with a bottom of the first electromagnet.

In an embodiment, each of the two water quality parameter detection mechanisms includes a detection box disposed on the top of the placement board, each of a front wall and a side wall of the detection box is embedded with monitoring sensors and underwater cameras, and the monitoring sensors and the underwater cameras are arranged at equal intervals and distributed alternately. The monitoring sensors at different positions are respectively configured to detect a water temperature, chlorophyll a, dissolved oxygen, salinity, turbidity, conductivity, a pH value, and an ammonia nitrogen value in the marine ranch.

In an embodiment, the top of the floating board defines placement grooves symmetrically arranged, and the placement grooves are distributed at intervals from the positioning rods. Connecting plates are disposed in the placement grooves by a threaded connection manner, and the connecting plates are configured to connect multiple floating boards together.

In an embodiment, the bottom of the sampling bucket is embedded with a second electromagnet, and the top of the placement board is provided with a second iron block, the second iron block is disposed behind the detection box. A top of the second iron block is in contact with a bottom of the second electromagnet. An outer surface of the sampling bucket is provided with a magnetic ring, an outer surface of the magnetic ring is in contact with an iron plate, and a side of the iron plate is connected to a back of the detection box.

In an embodiment, each of the front wall and the side wall of the detection box is provided with mesh frames by a threaded connection manner, and the mesh frame is located at outer sides of the monitoring sensors.

In an embodiment, a top wall of the sampling bucket is provided with a liquid level sensor, and a bottom of the liquid level sensor is in contact with a top of the perforated baffle. The liquid level sensor is configured to monitor whether the sampling bucket contains seawater or a time for collecting seawater by the sampling bucket.

In an embodiment, a bottom of the placement board is provided with a fixator, and the fixator is configured to secure the placement boards to seafloor.

In an embodiment, a deployment method of the neural network-based water quality monitoring device for the marine ranch is provided, and steps of the deployment method are as follows.

S1: locations and quantities of water quality monitoring points are reasonably determined based on a scale, a layout, and breeding requirements of the marine ranch, deployment locations near aquaculture zones, areas vulnerable to pollution, or key water confluence areas for deploying the neural network-based water quality monitoring device for the marine ranch are determined and a fixed deployment method or mobile deployment method is employed. The fixed deployment method for deploying the neural network-based water quality monitoring device for the marine ranch includes step as follows. Multiple sets of floating boards are placed around the marine ranch through connecting boards according to a size of the marine ranch.

S2: one or more sets of the connection mechanisms are mounted at the bottom of the floating board based on monitoring requirements, then the placement boards are attached to a lower end of each of the connection mechanisms, and mounting two sets of detection boxes on each of the placement board.

S3: subsequently, the placement boards are taken by a diver to seafloor of the marine ranch and securing the placement boards using a fixator.

S4: the various water quality parameters of the marine ranch are detected using the monitoring sensors in the detection boxes.

In an embodiment, in the S1, the fixed deployment method is capable of forming three different types of networks as needed: a star shaped network, a cluster shaped network, and a mesh shaped network.

Compared to the related art, the beneficial effects of the disclosure are as follows.

1. The disclosure monitors water surface environmental factors and collects underwater water quality parameters of the marine ranch through the host computer monitor. The collected water quality parameters are input into the neural network for analysis and processing, thereby achieving automatic recognition and classification of the water quality parameters. The data generated during the operation of the marine ranch are accumulated and integrated. By using cloud computing technology, the disclosure conducts in-depth analysis and mining of the internal and external relationships and objective laws between other objectives in the marine ranch and the water quality. This facilitates the determination of whether water pollution can be resolved at the source based on the identified relationships.

2. The disclosure is provided with the water quality parameter detection mechanism. When monitoring various water quality parameters of the marine ranch, the detection boxes are first mounted on the placement boards. Divers are then dispatched to stretch the connection mechanisms on the floating boards to an appropriate position. Next, the placement boards are secured to the appropriate position on the seafloor by using fixators. After that, multiple monitoring sensors inside the detection boxes can be used to detect various water quality parameters. The multi-source data detected are integrated to enhance the monitoring effectiveness. The underwater cameras are also mounted to monitor the seafloor conditions. Additionally, by synchronizing towed photography with global positioning system (GPS), the captured video images can be stitched together to form large-scale composite images, facilitating comprehensive water pollution monitoring.

3. The disclosure is provided with the sampling mechanism. When sampling the water quality of the marine ranch, the first step is to de-energize the first electromagnet, causing it to release the first iron block. Seawater then passes through the mesh plate, pushing up the sealing plug and entering the interior of the sampling bucket through the inlet hole. At this point, the liquid level sensor detects the entry of seawater and records the sampling time. After sampling is completed, the first electromagnet is energized to re-engage with the first iron block. The sampling bucket is then retrieved from the marine ranch via the connecting ropes for testing. This allows for convenient monitoring of water samples from different time periods or the same area within the same time period. The test results can be compared and analyzed with the data detected by the water quality parameter detection mechanism to improve the accuracy of water quality parameter detection.

The disclosure defines the placement grooves and includes the connecting plates. Before using the water quality monitoring mechanism, the scale, layout, and breeding requirements of the marine ranch are considered, and the positions and quantities of the floating boards are determined based on the size of the marine ranch. The connecting plates are then placed into the placement grooves and secured by a threaded connection manner. This allows two floating boards to be fixed together. Multiple connecting plates can be used to connect multiple floating boards according to the shape of the marine ranch.

Figure 1:
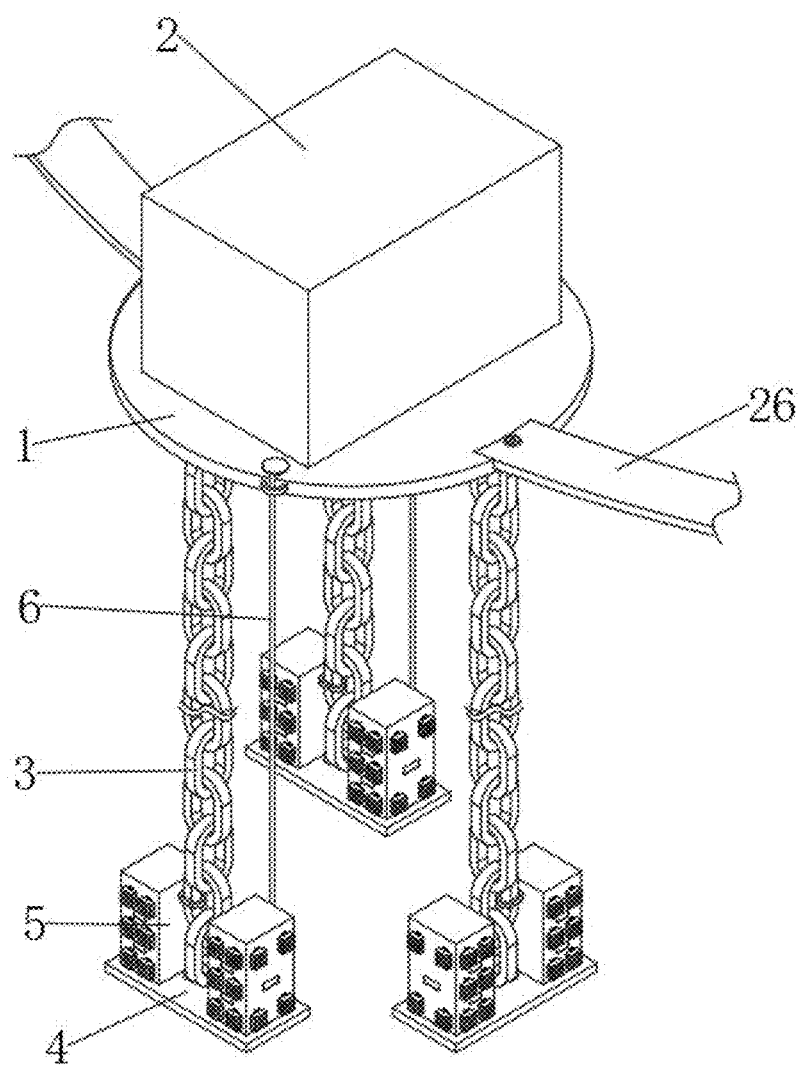
FIG. 1 illustrates an overall schematic structural diagram of the disclosure.

DESCRIPTION OF REFERENCE NUMERALS 1. floating board; 2. host computer monitor; 3. connection mechanism; 4. placement board; 5. water quality parameter detection mechanism; 6. sampling mechanism; 7. hook ring; 8. positioning rod; 9. connecting rope; 10. sampling bucket; 11. liquid level sensor; 12. mesh plate; 13. sealing plug; 14. first iron block; 15. first electromagnet; 16. perforated baffle; 17. second electromagnet; 18. magnetic ring; 19. second iron block; 20. detection box; 21. mesh frame; 22. monitoring sensor; 23. underwater camera; 24. fixator; 25. placement groove; 26. connecting plate; 27. sampling hole; 28. groove.

DETAILED DESCRIPTION OF EMBODIMENTS

The following description, in conjunction with the attached drawings in the embodiments of the disclosure, the technical solutions in the embodiments of the disclosure will be described clearly and completely. It should be apparent that the described embodiments are merely a part of the embodiments of the disclosure, and not all of them. Any other embodiments obtained by those skill in the art without making inventive efforts, based on the embodiments of the disclosure, are within the scope of protection of the disclosure.

In the description of the disclosure, it should be noted that the terms "up," "down," "inside," "outside," "front end," "rear end," "both ends," "an end," "another end," and so on, indicate directions or positional relationships based on the orientation shown in the attached drawings. These terms are used merely for the convenience of describing the disclosure and simplifying the description, rather than indicating or implying that the device or component must have a specific orientation, be constructed and operated in a specific direction. Therefore, these terms should not be construed as limitations on the disclosure. Additionally, the terms "first" and "second" are used solely for descriptive purposes and should not be interpreted as indicating or implying relative importance.

In the description of the disclosure, it should be noted that unless otherwise explicitly specified and limited, the terms "mount," "be provided with," "connect," and so on, should be understood in a broad sense. For example, "connect" can refer to a fixed connection, a detachable connection, or an integral connection; it can be a mechanical connection or an electrical connection; it can be a direct connection or an indirect connection through an intermediary. It can also refer to the internal connection between two components. For those skilled in the art, the specific meanings of the above terms in the context of the disclosure can be understood according to the specific situation.

As shown in FIGS. 1, 8 and 13-14, a neural network-based water quality monitoring device for marine ranch is provided, and the device includes a floating board 1 and a host computer monitor 2. The host computer monitor 2 is disposed on a top of the floating board 1, and the host computer monitor 2 is provided with a water quality monitoring system, and the water quality monitoring system is configured to collect water quality parameters of the marine ranch and analyze the collected water quality parameters. The water quality monitoring system includes an environmental monitoring unit, a data acquisition unit, a wireless transmission unit, and a data integration unit. The environmental monitoring unit is configured to use a hyperspectral water quality multiparameter monitor to monitor data of a large number of continuous spectral segments within a target wavelength range in water body in the marine ranch to monitor in real time data comprising a concentration of dissolved substances in the water body, growth of algae, water pollution, water color, and presence of solid floating objects on water surface. The data acquisition unit is configured to use a data collector to collect the monitored data from the environmental monitoring unit. The wireless transmission unit includes a coordinator, and the coordinator is configured to upload the collected data to a neural network for analysis and processing. The data integration unit is configured to use a central processor to accumulate and integrate data generated during an operation of the marine ranch, and employs cloud computing technology to conduct in-depth analysis and mining of the intrinsic relationships and objective laws among various objectives in the marine ranch. Connection mechanisms 3 are uniformly distributed on a bottom of the floating board 1, a bottom of each of the connection mechanisms 3 is provided with a placement board 4. A top of the placement board 4 is provided with two water quality parameter detection mechanisms 5 symmetrically arranged, and the two water quality parameter detection mechanisms 5 are disposed at two sides of the connection mechanisms 3. A back side of the two water quality parameter detection mechanisms 5 is provided with a sampling mechanism 6, and the sampling mechanism 6 is configured to collect water samples from different time periods. A bottom of the placement board 4 is provided with a fixator 24, and the fixator 24 is configured to secure the placement boards 4 to seafloor.

In addition, in water quality monitoring of the marine ranch, multiple detection boxes 20 are deployed to monitor different target areas. Each of the detection boxes 20 can integrate up to 10 different types of monitoring sensors 22. Data from the same type of monitoring sensors 22 on different detection boxes 20 within the same marine ranch are fused. This approach can, to some extent, avoid the impact of partial monitoring sensor 22 failures or deviations on monitoring values. During the water quality monitoring process, the hyperspectral water quality multiparameter monitor analyzes the spectral characteristics of light after its interaction with dissolved substances in the water body by emitting and receiving the light at different wavelengths. This allows for the inference of the types and concentrations of dissolved substances, enabling real-time and continuous monitoring of multiple chemical components and pollutant concentrations in the water body, such as a distribution of chlorophyll a. By analyzing the spectral characteristics of the water body, it is also possible to assess water color, water transparency, and presence of solid floating objects on water surface of the water body. Subsequently, the host computer monitor 2 is configured to monitor water surface environmental factors and collects underwater water quality parameters. The collected underwater water quality parameters are then input into the neural network via the coordinator for analysis and processing, thereby achieving automatic recognition and classification of the collected underwater water quality parameters. Data generated during the operation of the marine ranch are accumulated and integrated. Using cloud computing technology, in-depth analysis and mining are conducted to explore the internal and external relationships and objective laws between other objectives in the marine ranch and water quality. This facilitates the determination of whether water pollution can be resolved at the source based on the identified relationships.

In an embodiment, as shown in FIGS. 1-3 and 6, the device includes the water quality parameter detection mechanisms 5. Each of the water quality parameter detection mechanisms 5 includes a detection box 20 disposed on the top of the placement board 4, each of a front wall and a side wall of the detection box 20 is embedded with monitoring sensors 22 and underwater cameras 23, and the monitoring sensors 22 and the underwater cameras 23 are arranged at equal intervals and distributed alternately. The monitoring sensors 22 at different positions are respectively configured to detect a water temperature, chlorophyll a, dissolved oxygen, salinity, turbidity, conductivity, a pH value, and an ammonia nitrogen value in the marine ranch. Each of the front wall and the side wall of the detection box 20 is provided with mesh frames 21 by a threaded connection manner, and the mesh frame 21 is located at outer sides of the monitoring sensors 22.

Furthermore, by deploying multiple sets of detection boxes 20 within the marine ranch, the monitoring sensors 22 on different detection boxes 20 can measure various water quality parameters at different locations within the same marine ranch. These parameters include the water temperature, the chlorophyll a, the dissolved oxygen, the salinity, the turbidity, the conductivity, the nitrite content, the pH value, and the ammonia nitrogen value. The data from the same type of monitoring sensors 22 on different detection boxes 20 within the same marine ranch are integrated to enhance the precision and effectiveness of data detection. Additionally, the underwater cameras 23 are disposed to monitor the conditions on the seafloor. Towed photography synchronized with GPS can also be used to stitch captured video images into large-scale composite images. This facilitates comprehensive monitoring of water pollution.

In an embodiment, as shown in FIGS. 1, 3, 4 and 5, the sampling mechanisms 6 includes a hook ring 7 disposed on an outer surface of the floating board 1, a top of the floating board 1 is provided with positioning rods 8, and the positioning rods 8 are disposed at an outer side of the host computer monitor 2. A longitudinal section of each of the positioning rods 8 is T-shaped, and outer surfaces of the positioning rods 8 are wound with connecting ropes 9, an end of a corresponding one of the connecting ropes 9 passes through the hook rings 7 and is connected to a sampling bucket 10. A bottom of the sampling bucket 10 defines a sampling hole 27, a mesh plate 12 is disposed in the sampling hole 27. The bottom of the sampling bucket 10 defines a groove 28, and the groove 28 is connected to the sampling hole 27. A sealing plug 13 is disposed in the groove 28, a bottom of the sealing plug 13 is in contact with a top of the mesh plate 12. A perforated baffle 16 is disposed in the sampling bucket 10, and the perforated baffle 16 is configured to position the sealing plug 13. A bottom of the sealing plug 13 is embedded with a first electromagnet 15, the bottom of the groove 28 is embedded with a first iron block 14, and tops of the first iron block 14 is in contact with bottoms of the first electromagnet 15. The liquid level sensor 11 is configured to monitor whether the sampling bucket 10 contains seawater or a time for collecting the seawater by the sampling bucket 10.

In addition, when performing the sampling operations, the first electromagnet 15 is first de-energized to release the first iron block 14. The sealing plug 13 then moves upward under buoyancy. Once the sealing plug 13 protrudes through the inlet hole, it is positioned by the perforated baffle 16. At this point, the seawater enters the interior of the sampling bucket 10 through the groove 28 and the perforated baffle 16. The liquid level sensors 11 detect an entry of seawater and record the sampling time. After sampling is completed, the first electromagnet 15 is energized, causing it to attract the first iron block 14 under magnetic force and re-establish contact. This action seals the inlet hole with the sealing plug 13. The connecting ropes 9 are then detached from the positioning rods 8, and the connecting ropes 9 are pulled upward. Before pulling, the second electromagnet 17 is de-energized. This allows the sampling bucket 10 to be retrieved from the marine ranch for water quality sampling and testing operations.

Figure 7:
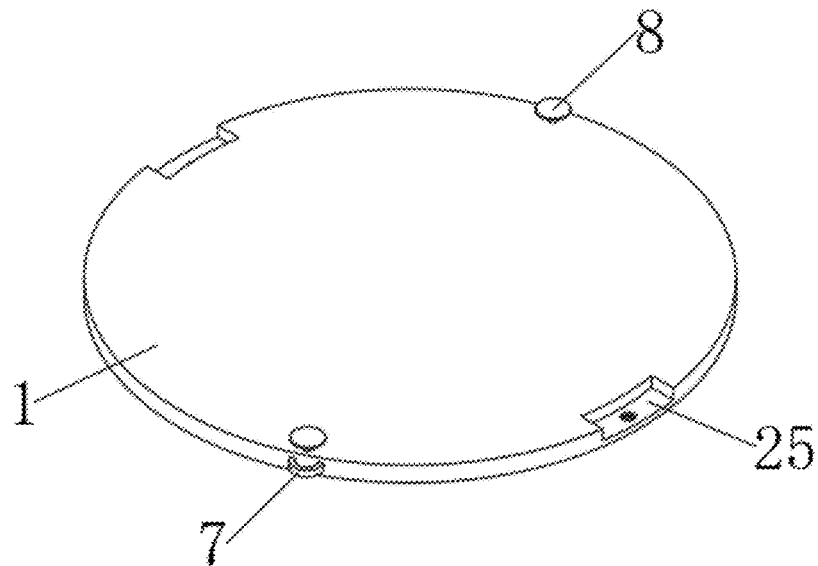
FIG. 7 illustrates a schematic diagram of an assembly structure of a floating board in the disclosure.
Figure 8:
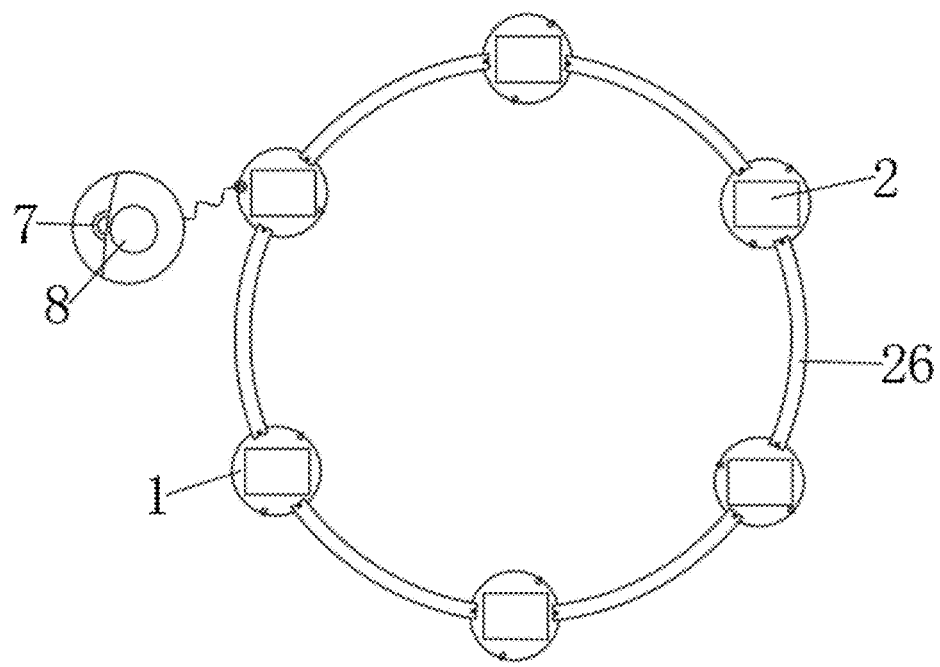
FIG. 8 illustrates a schematic diagram of a connection between multiple sets of floating plates in the disclosure.
Figure 9:
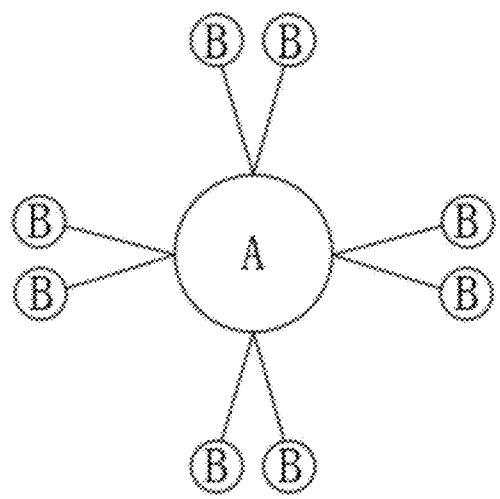
FIG. 9 illustrates a schematic diagram of a star shaped network in the disclosure.
Figure 10:
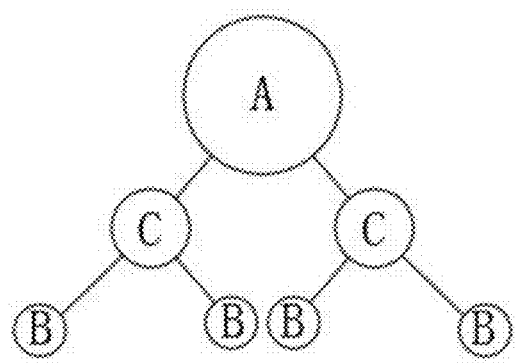
FIG. 10 illustrates a schematic diagram of a cluster shaped network in the disclosure.
Figure 11:
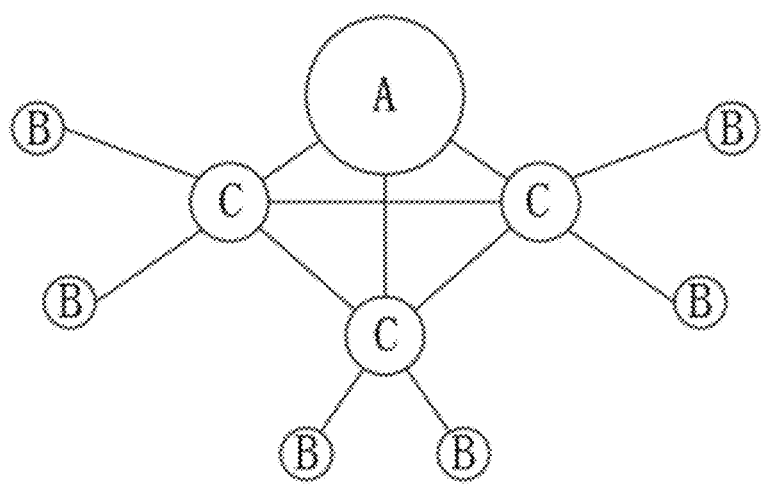
FIG. 11 illustrates a schematic diagram of a mesh shaped network in the disclosure.
Figure 12:
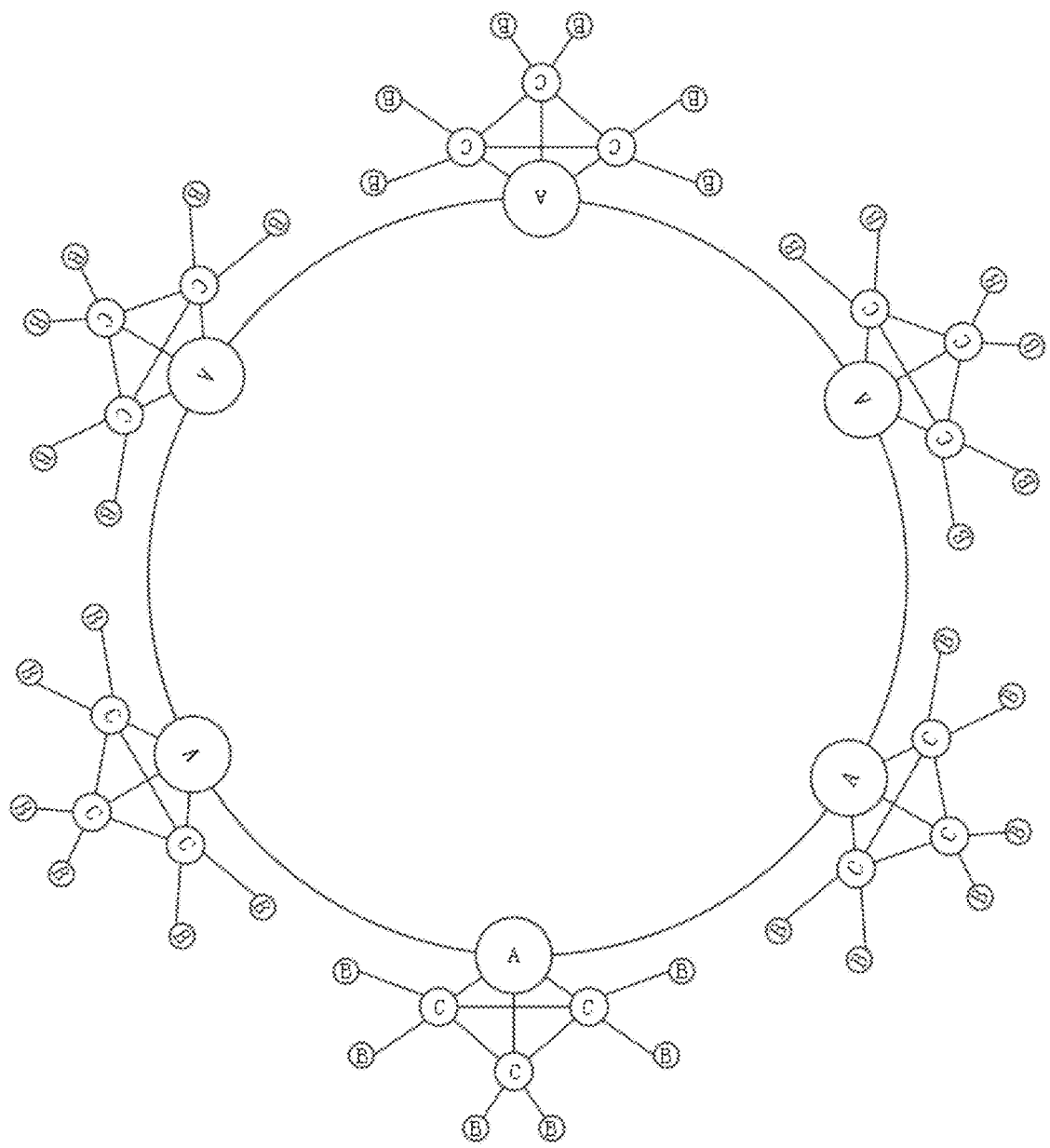
FIG. 12 illustrates a schematic diagram of a connection of multiple mesh shaped networks in the disclosure.
Figure 13:
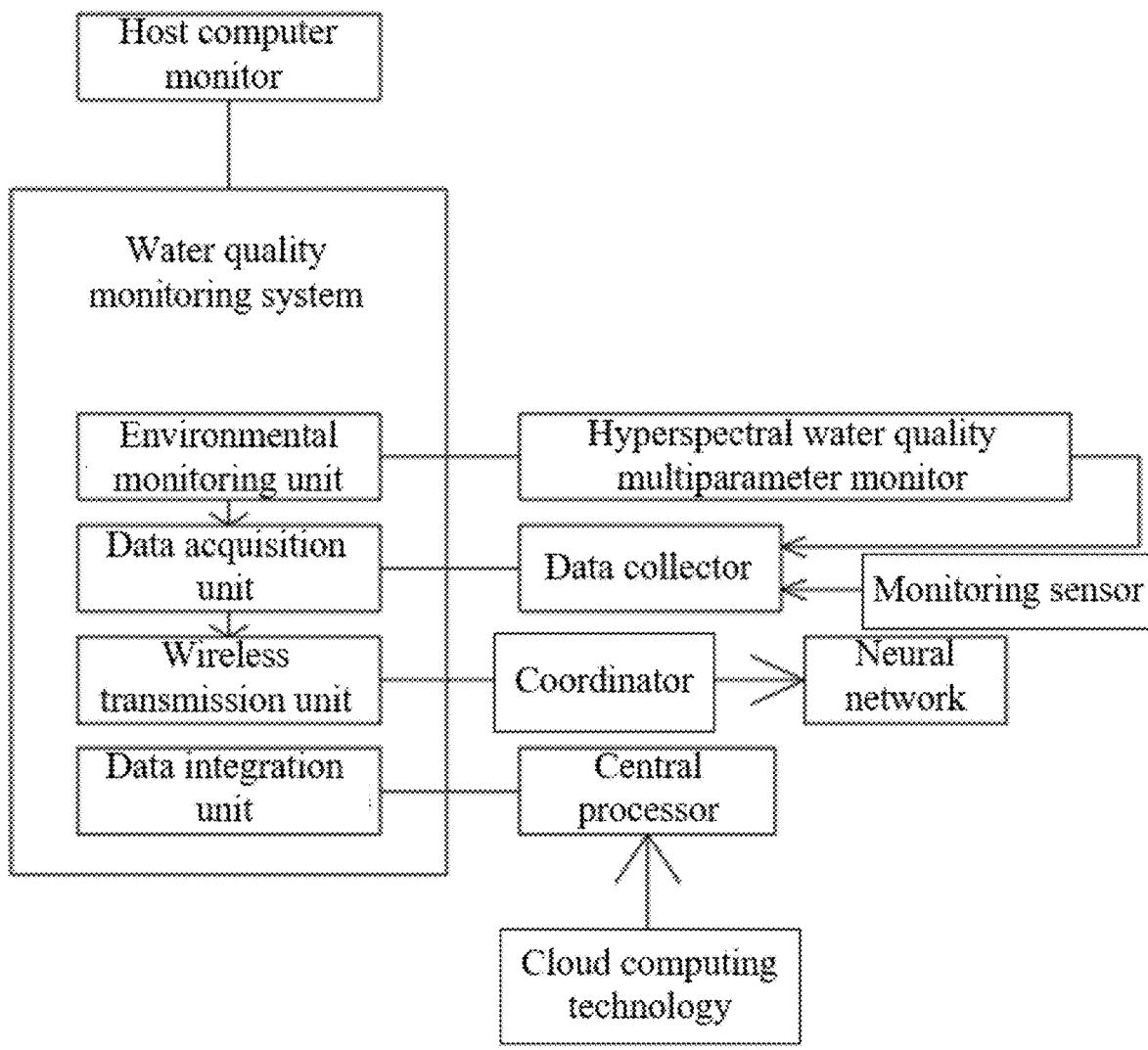
FIG. 13 illustrates a composition diagram of a water quality monitoring system in the disclosure.
Figure 14:
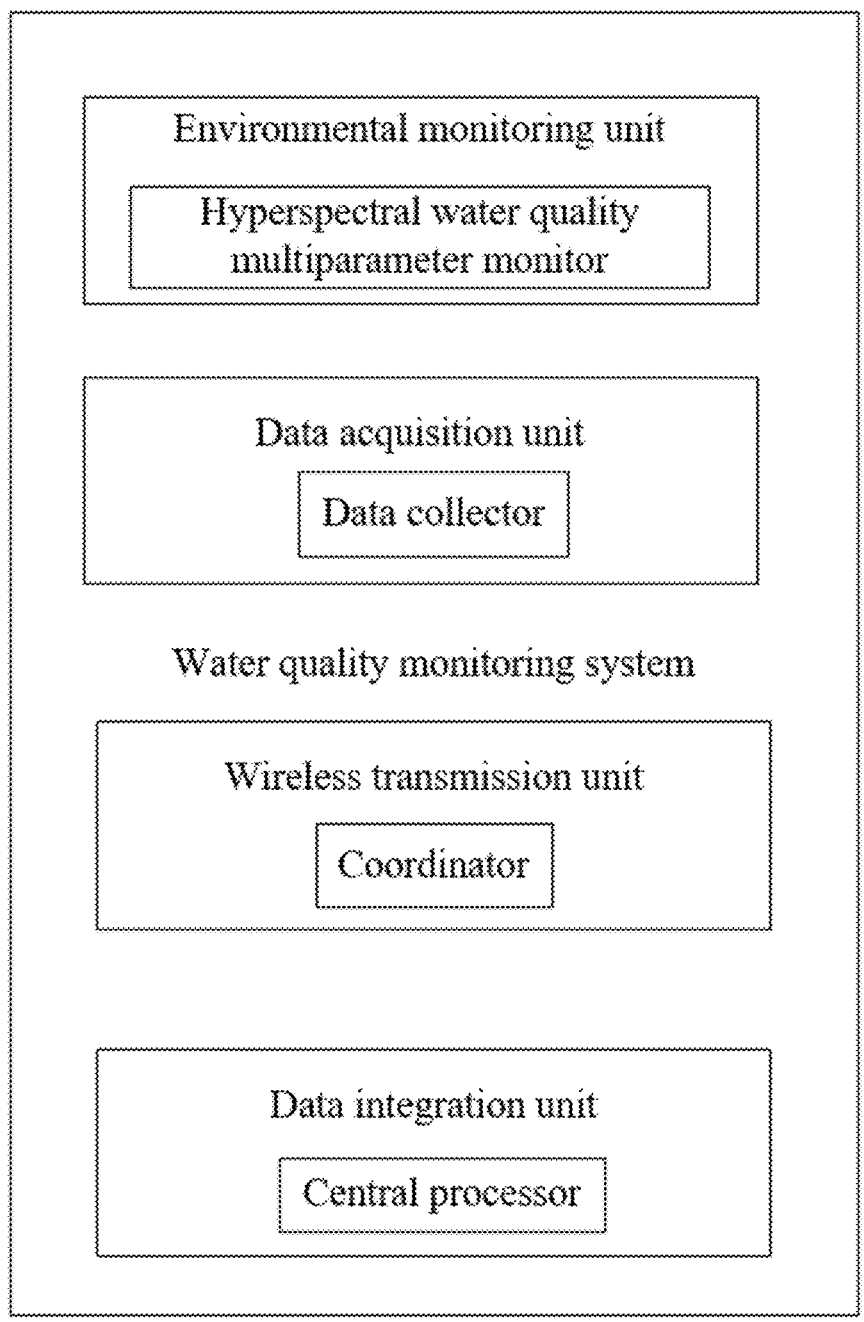
FIG. 14 illustrates a schematic diagram of the water quality monitoring system in the disclosure.

In an embodiment, as shown in FIGS. 7 and 8, in the device, the top of the floating board 1 defines placement grooves 25 symmetrically arranged, and the placement grooves are distributed at intervals from the positioning rods 8. Connecting plates 26 are disposed in the placement grooves 25 by a threaded connection manner, and the connecting plates 26 are configured to connect multiple floating boards 1 together.

Furthermore, before using the water quality monitoring device, the positions and quantities of the floating boards 1 are first determined based on the scale, layout, and breeding requirements of the marine ranch. The connecting plates 26 are then placed into the placement grooves 25 and secured by the threaded connection manner. This allows two sets of floating boards 1 to be connected together.

Figure 2:
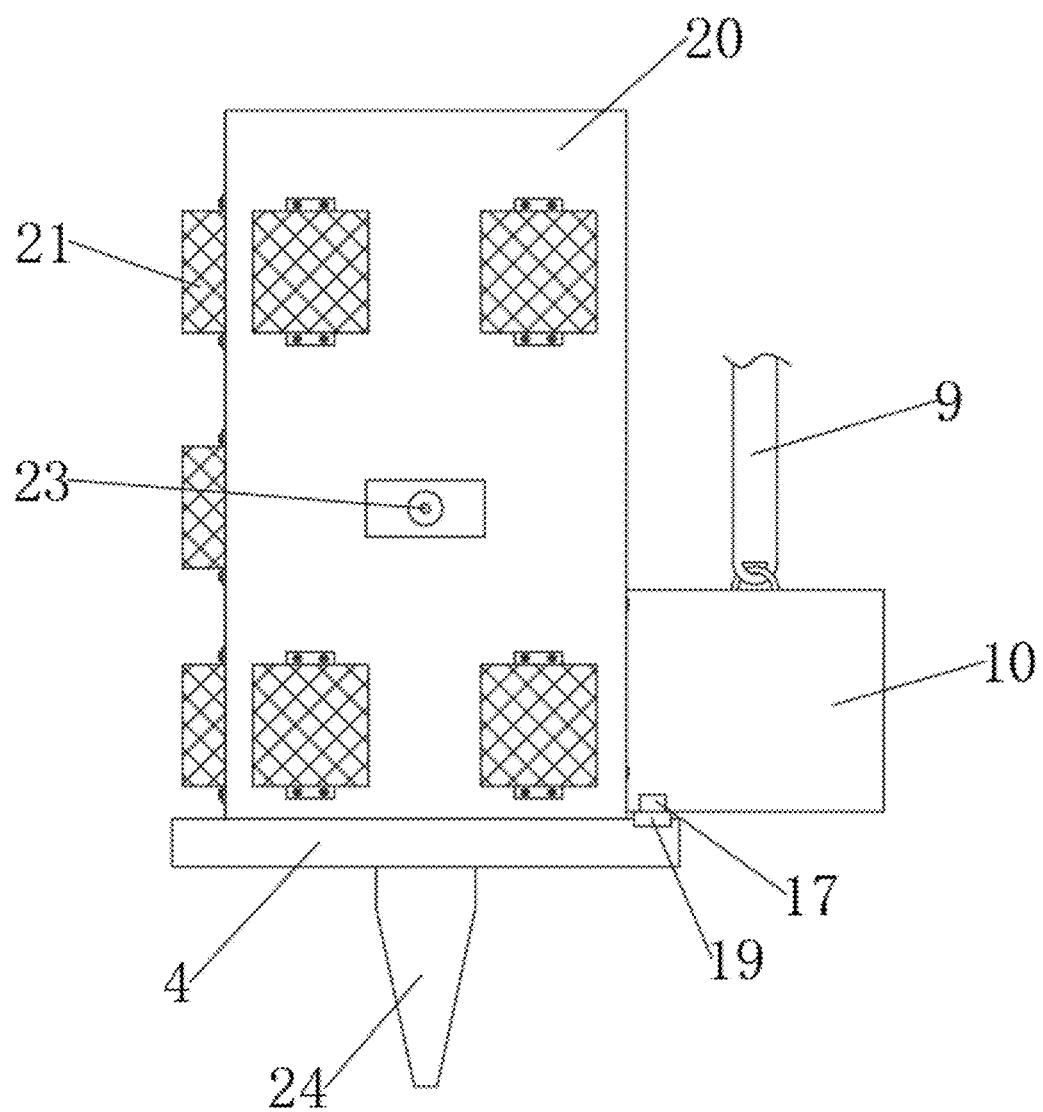
FIG. 2 illustrates a schematic diagram of a planar assembly structure of a detection box in the disclosure.
Figure 3:
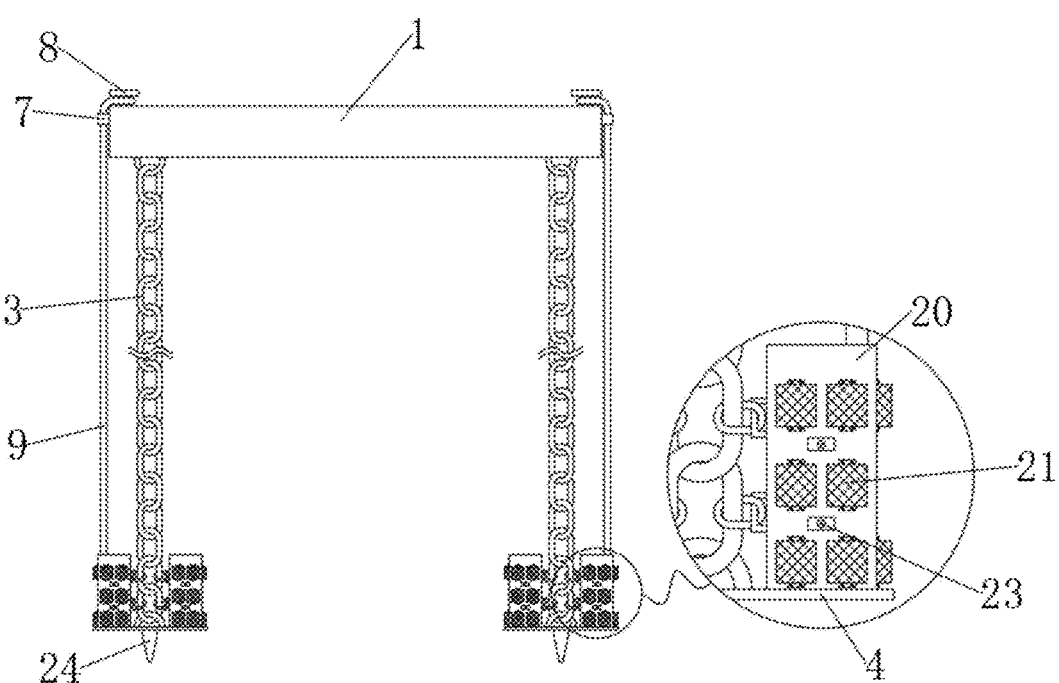
FIG. 3 illustrates a schematic diagram of a planar assembly structure of connection mechanisms and placement boards in the disclosure.
Figure 4:
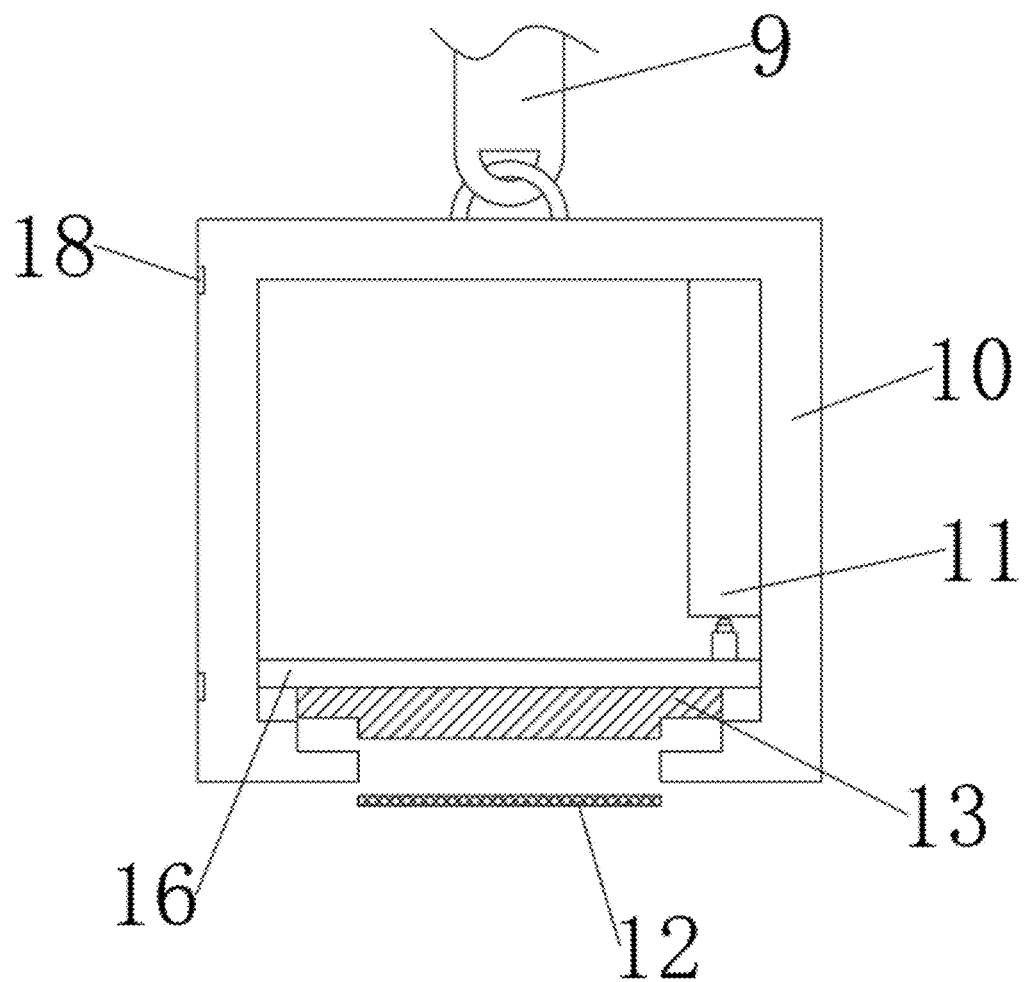
FIG. 4 illustrates a schematic diagram of a planar assembly structure of a sampling bucket in the disclosure.
Figure 5:
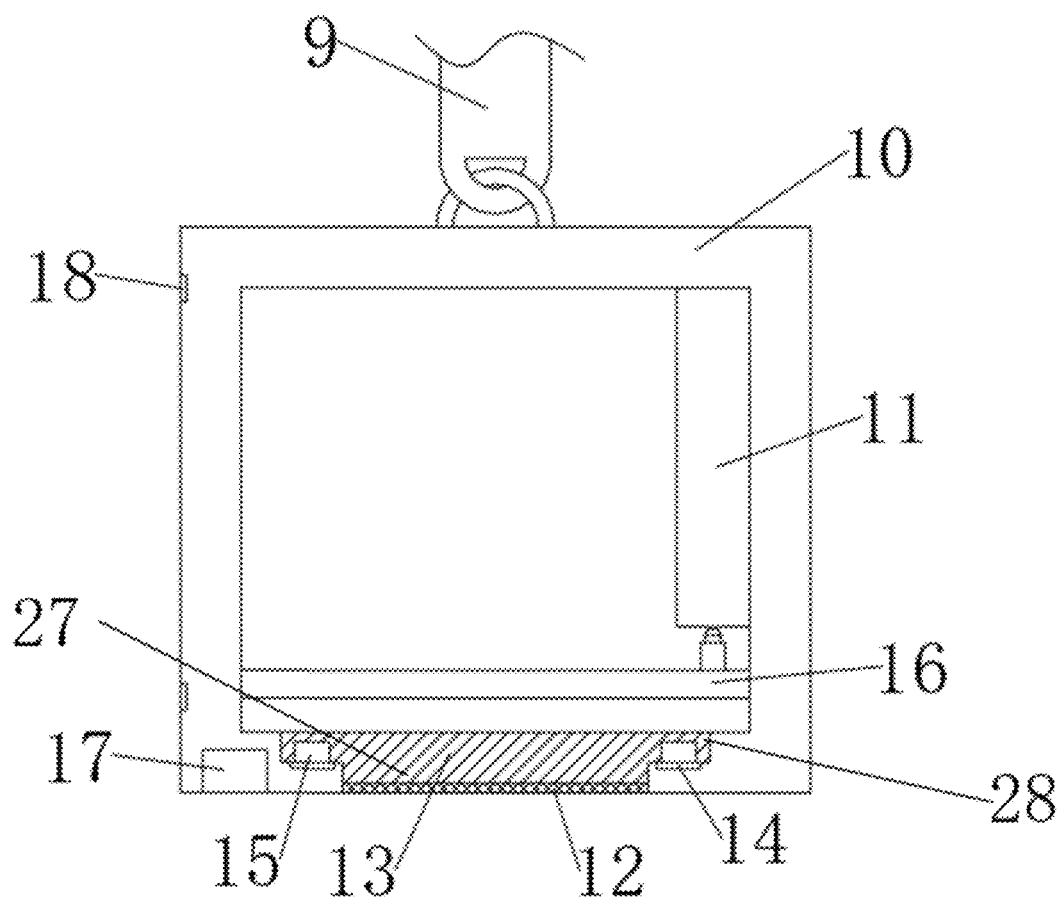
FIG. 5 illustrates a schematic diagram of a planar assembly structure of a sealing plug and a perforated baffle in the disclosure.
Figure 6:
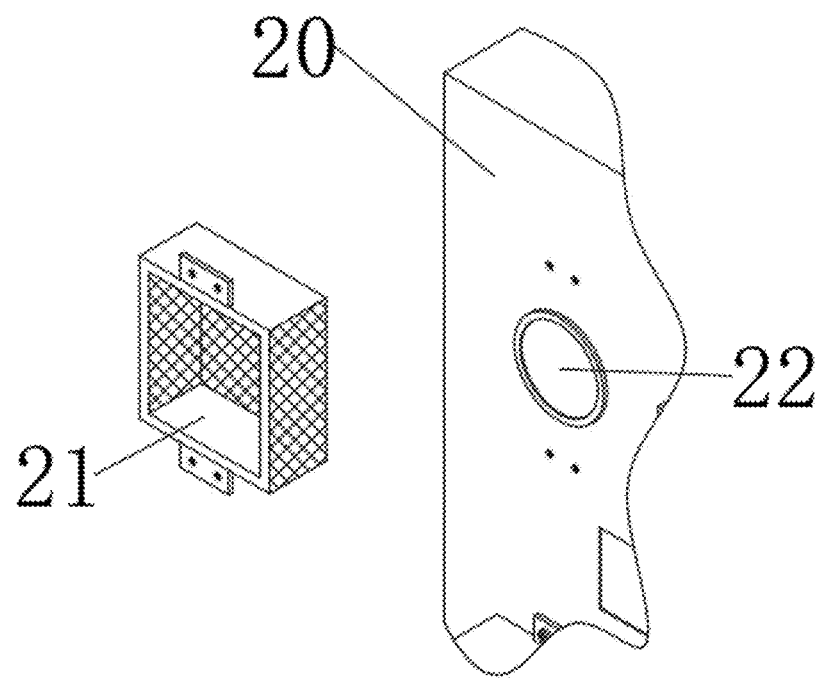
FIG. 6 illustrates a schematic diagram of an assembly structure of a mesh frame in the disclosure.

In an embodiment, as shown in FIG. 2, the bottom of the sampling bucket 10 is embedded with a second electromagnet 17, and the top of the placement board 4 is provided with a second iron block 19, the second iron block 19 is disposed behind the detection box 20. A top of the second iron block 19 is in contact with a bottom of the second electromagnet 17. An outer surface of the sampling bucket 10 is provided with a magnetic ring 18, an outer surface of the magnetic ring 18 is in contact with an iron plate, and a side of the iron plate is connected to a back of the detection box 20.

Furthermore, when retrieving the sampling bucket 10 from the marine ranch, the second electromagnet 17 is first de-energized to release the second iron block 19. Then, by pulling the connecting ropes 9 upward, the magnetic ring 18 on the sampling bucket 10 is separated from the iron plate on the detection box 20. This allows the sampling bucket 10 to be removed from the marine ranch for water quality testing. The test results are then compared and analyzed with the results from the same sampling location to assess the sensitivity of the monitoring sensors 22.

In an embodiment, as shown in FIGS. 9-12, a deployment method of the neural network-based water quality monitoring device for the marine ranch is provided, and the deployment method includes steps as follows.

S1: locations and quantities of water quality monitoring points are reasonably determined based on a scale, a layout, and breeding requirements of the marine ranch, deployment locations near aquaculture zones, areas vulnerable to pollution, or key water confluence areas are determined, and a fixed deployment method or a mobile deployment method is employed. The fixed deployment method includes step as follows. Multiple sets of floating boards 1 are placed around the marine ranch through connecting boards 26 according to a size of the marine ranch.

S2: one or more sets of the connection mechanisms 3 are mounted at the bottom of the floating board 1 based on monitoring requirements, then the placement boards 4 are attached to a lower end of each of the connection mechanisms 3, and mounting two sets of detection boxes 20 on each of the placement board 4.

S3: subsequently, the placement boards 4 are taken by a diver to seafloor of the marine ranch and securing the placement boards 4 using a fixator.

S4: the various water quality parameters of the marine ranch are detected using the monitoring sensors 22 in the detection boxes 20.

In the S1, the fixed deployment method is capable of forming three different types of networks as needed: star shaped network, cluster shaped network, and mesh shaped network.

Furthermore, the host computer monitor 2 is powered by a battery and floats on the monitoring water area via the floating board 1. the host computer monitor 2 collects data from various sensors using a data collector and transmits the processed digital signals to the coordinator in either a single-hop or multi-hop manner. The data is then sent to the central processor via a serial port for real-time monitoring of seawater ecological parameters. A represents the coordinator, B represents the monitoring sensor 22, and C represents a router. A star network consists of one coordinator and multiple monitoring sensors 22. A cluster network includes one coordinator, multiple routers, and multiple monitoring sensors 22. The mesh network includes the same deployment method as the star network, but it allows all routing nodes to communicate directly, reducing network propagation delay and increasing reliability. In the actual deployment process, multiple coordinators within the same marine ranch can be connected together, enabling data communication between different areas of the same marine ranch and expanding the scope of water quality monitoring.

A working principal of the disclosure is as follows.

First, an appropriate number of floating boards 1 is select based on the shape and size of the marine ranch. Then, each set of floating boards 1 are connected together using connecting plates 26. Next, according to the usage requirements, the detection boxes 20 are mounted on the placement boards 4 and the sampling buckets 10 are secured to the detection boxes 20. After that, an end of the connecting rope 9 passes through the hook ring 7 and wind it around the positioning rod 8. Subsequently, the diver takes the placement boards 4 to the seafloor and secure it in the appropriate position using the fixators 24. After this, the environmental monitoring unit and monitoring sensors 22 can be used to detect water surface environmental parameters and underwater water quality parameters. The collected water quality parameters is then uploaded to the neural network via the coordinator for analysis and processing, thereby achieving automatic recognition and classification of water quality parameters.

When performing the sampling operations, the first electromagnet 15 is first de-energized to release the first iron block 14. The sealing plug 13 then moves upward under buoyancy. At this point, the seawater enters the interior of the sampling bucket 10 through the groove 28 and the perforated baffle 16. After sampling is completed, the first electromagnet 15 is energized, causing it to attract the first iron block 14 under magnetic force and re-establish contact. This action seals the inlet hole with the sealing plug 13. The connecting ropes 9 are then detached from the positioning rods 8, and the connecting ropes 9 are pulled upward. Before pulling, the second electromagnet 17 is de-energized. This allows the sampling bucket 10 to be retrieved from the marine ranch for water quality sampling and testing operations.

For those skilled in the art, it is apparent that the disclosure is not limited to the details of the above-described embodiments, and that the disclosure can be embodied in other specific forms without departing from the spirit or essential characteristics of the disclosure. Therefore, in every respect, the embodiments should be regarded as illustrative and not restrictive. The scope of the disclosure is defined by the appended claims rather than by the foregoing description. Accordingly, all changes that come within the meaning and range of equivalents of the claims are intended to be embraced within the scope of the disclosure. No reference signs in the claims should be construed as limiting the scope of the claims.

What is claimed is:

1. A neural network-based water quality monitoring device for a marine ranch, comprising:

a floating board (1) and a host computer monitor (2), wherein the host computer monitor (2) is disposed on a top of the floating board (1), and the host computer monitor (2) is provided with a water quality monitoring system, and the water quality monitoring system is configured to collect water quality parameters of the marine ranch and analyze the collected water quality parameters;

wherein the water quality monitoring system comprises an environmental monitoring unit, a data acquisition unit, a wireless transmission unit, and a data integration unit; the environmental monitoring unit is configured to use a hyperspectral water quality multiparameter monitor to monitor continuous spectral segments within a target wavelength range in water body in the marine ranch to monitor in real time data comprising a concentration of dissolved substances in the water body, growth of algae, water pollution, water color, and presence of solid floating objects on a water surface of the marine ranch; the data acquisition unit is configured to use a data collector to collect the monitored data from the environmental monitoring unit; the wireless transmission unit comprises a coordinator, and the coordinator is configured to upload the collected data to a neural network for analysis and processing; and the data integration unit is configured to use a central processor to accumulate and integrate data generated during an operation of the marine ranch, and employ cloud computing technology to conduct analysis and mining of intrinsic relationships and objective laws among objectives in the marine ranch;

wherein connection mechanisms (3) are uniformly distributed on a bottom of the floating board (1), a bottom of each of the connection mechanisms (3) is provided with a placement board (4); a top of the placement board (4) is provided with two water quality parameter detection mechanisms (5) symmetrically arranged, and the two water quality parameter detection mechanisms (5) are disposed at two sides of the connection mechanisms (3); a back side of the two water quality parameter detection mechanisms (5) is provided with a sampling mechanism (6), and the sampling mechanism (6) is configured to collect water samples from different time periods; and wherein the sampling mechanism (6) comprises a hook ring (7) disposed on an outer surface of the floating board (1), a top of the floating board (1) is provided with positioning rods (8), and the positioning rods (8) are disposed at an outer side of the host computer monitor (2); a longitudinal section of each of the positioning rods (8) is T-shaped, and outer surfaces of the positioning rods (8) are wound with connecting ropes (9), an end of a corresponding one of the connecting ropes (9) passes through the hook ring (7) and is connected to a sampling bucket (10); a bottom of the sampling bucket (10) defines a sampling hole (27), a mesh plate (12) is disposed in the sampling hole (27); the bottom of the sampling bucket (10) defines a groove (28), and the groove (28) is connected to the sampling hole (27); a sealing plug (13) is disposed in the groove (28), a bottom of the sealing plug (13) is in contact with a top of the mesh plate (12); a perforated baffle (16) is disposed in the sampling bucket (10), and the perforated baffle (16) is configured to position the sealing plug (13); a bottom of the sealing plug (13) is embedded with a first electromagnet (15), the bottom of the groove (28) is embedded with a first iron block (14), and a top of the first iron block is in contact with a bottom of the first electromagnet (15).

2. The neural network-based water quality monitoring device for the marine ranch as claimed in claim 1, wherein each of the two water quality parameter detection mechanisms (5) comprises a detection box (20) disposed on the top of the placement board (4), each of a front wall and a side wall of the detection box (20) is embedded with monitoring sensors (22) and underwater cameras (23), and the monitoring sensors (22) and the underwater cameras (23) are arranged at equal intervals and distributed alternately; the monitoring sensors (22) at different positions are respectively configured to detect a water temperature, chlorophyll a, dissolved oxygen, salinity, turbidity, conductivity, a pH value, and an ammonia nitrogen value in the marine ranch.

3. The neural network-based water quality monitoring device for the marine ranch as claimed in claim 2, wherein the top of the floating board (1) defines placement grooves (25) symmetrically arranged, and the placement grooves (25) are distributed at intervals from the positioning rods (8); connecting plates (26) are disposed in the placement grooves (25) by a threaded connection manner, and the connecting plates (26) are configured to connect multiple floating boards (1) together.

4. The neural network-based water quality monitoring device for the marine ranch as claimed in claim 3, wherein a bottom of the placement board (4) is provided with a fixator (24), and the fixator (24) is configured to secure the placement boards (4) to seafloor.

5. A deployment method of the neural network-based water quality monitoring device for the marine ranch as claimed in claim 4, the deployment method comprising:

S1: reasonably determining locations and quantities of water quality monitoring points based on a scale, a layout, and breeding requirements of the marine ranch, determining deployment locations near aquaculture zones, areas vulnerable to pollution, or key water confluence areas for deploying the neural network-based water quality monitoring device for the marine ranch, and employing a fixed deployment method or a mobile deployment method for deploying the neural network-based water quality monitoring device for the marine ranch; wherein the fixed deployment method comprises:

placing multiple sets of floating boards (1) around the marine ranch through connecting boards (26) according to a size of the marine ranch;

S2: mounting one or more sets of the connection mechanisms (3) at the bottom of the floating board (1) based on monitoring requirements, attaching the placement board (4) to a lower end of each of the connection mechanisms (3), and mounting two sets of detection boxes (20) on the placement board (4);

S3: subsequently, taking, by a diver, the placement board (4) to seafloor of the marine ranch and securing the placement board (4) using a fixator (24); and S4: detecting the water quality parameters of the marine ranch using the monitoring sensors (22) in the detection boxes (20).

6. The deployment method as claimed in claim 5, wherein, in the S1, the fixed deployment method is capable of forming three different types of networks as needed: a star shaped network, a cluster shaped network, and a mesh shaped network.

7. The neural network-based water quality monitoring device for the marine ranch as claimed in claim 2, wherein each of the front wall and the side wall of the detection box (20) is provided with mesh frames (21) by a threaded connection manner, and the mesh frame (21) is located at outer sides of the monitoring sensors (22).

8. The neural network-based water quality monitoring device for the marine ranch as claimed in claim 1, wherein the bottom of the sampling bucket (10) is embedded with a second electromagnet (17), and the top of the placement board (4) is provided with a second iron block (19), the second iron block (19) is disposed behind the detection box (20); a top of the second iron block (19) is in contact with a bottom of the second electromagnet (17); an outer surface of the sampling bucket (10) is provided with a magnetic ring (18), an outer surface of the magnetic ring (18) is in contact with an iron plate, and a side of the iron plate is connected to a back of the detection box (20).

9. The neural network-based water quality monitoring device for the marine ranch as claimed in claim 1, wherein a top wall of the sampling bucket (10) is provided with a liquid level sensor (11), and a bottom of the liquid level sensor (11) is in contact with a top of the perforated baffle (16); the liquid level sensor (11) is configured to monitor whether the sampling bucket (10) contains seawater or a time for collecting seawater by the sampling bucket (10).

* * * * *